(12) United States Patent
Segel et al.

(10) Patent No.: US 10,568,691 B2
(45) Date of Patent: Feb. 25, 2020

(54) METHOD AND APPARATUS FOR STIMULATING CELLULITE REDUCTION WITH FEMTOSECOND LASER IRRADIATION

(71) Applicant: LaserStim, Inc., Plano, TX (US)

(72) Inventors: Kim Robin Segel, Plano, TX (US); Jeff Adelglass, Plan, TX (US)

(73) Assignee: LaserStim, Inc., Plano, TX (US)

( * ) Notice: Subject to any disclaimer, the term of this patent is extended or adjusted under 35 U.S.C. 154(b) by 0 days.

(21) Appl. No.: 15/785,118

(22) Filed: Oct. 16, 2017

(65) Prior Publication Data

US 2018/0111000 A1  Apr. 26, 2018

Related U.S. Application Data

(60) Provisional application No. 62/408,499, filed on Oct. 14, 2016.

(51) Int. Cl.
| | | |
|---|---|---|
| *A61B 18/18* | (2006.01) | |
| *A61B 18/20* | (2006.01) | |
| *A61N 5/06* | (2006.01) | |
| A61B 17/00 | (2006.01) | |
| A61B 18/00 | (2006.01) | |
| A61N 5/067 | (2006.01) | |

(52) U.S. Cl.
CPC .......... *A61B 18/203* (2013.01); *A61N 5/0616* (2013.01); *A61B 2017/00769* (2013.01); *A61B 2018/00452* (2013.01); *A61B 2018/00464* (2013.01); *A61B 2018/202* (2013.01); *A61B 2018/2065* (2013.01); *A61N 2005/067* (2013.01); *A61N 2005/0644* (2013.01)

(58) Field of Classification Search
CPC ........ A61B 18/203; A61B 2017/00769; A61B 2018/00452; A61B 2018/00464; A61B 2018/202; A61B 2018/2056; A61N 5/0616; A61N 2005/0626; A61N 2005/00644; A61N 2005/00645; A61N 2005/067
USPC .......................................................... 607/89
See application file for complete search history.

(56) References Cited

U.S. PATENT DOCUMENTS

2012/0253334 A1* 10/2012 Liu ...................... A61B 18/203
606/9

* cited by examiner

*Primary Examiner* — Aaron F Roane

(57) ABSTRACT

The invention provides a method and apparatus for stimulating cellulite reduction using a femtosecond diode laser irradiation system. The system comprises a femtosecond diode laser capable of generating laser light that has a wavelength of 1000 nm-10,000 nm, a power level of 300 mw-5 W, and a pulse duration of less than 1 picosecond. A light-emitting device is coupled to the diode laser by means of flexible waveguide and is held over the skin. The device may be a handheld wand or an area pad comprising a plurality of light-emitting lenses on a surface of the pad. Laser setting controls are set to achieve a depth of photon absorption into the skin to reach subcutaneous adipose tissue.

12 Claims, 4 Drawing Sheets

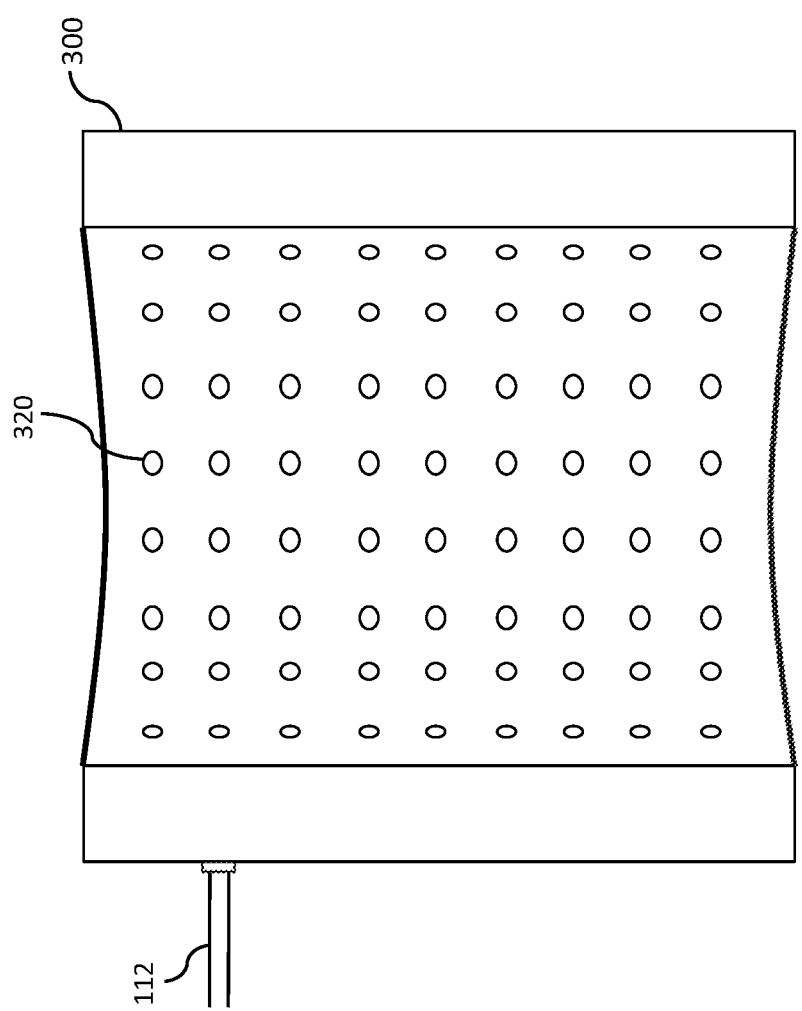

METHOD AND APPARATUS FOR STIMULATING CELLULITE REDUCTION WITH FEMTOSECOND LASER IRRADIATION

CROSS-REFERENCE TO RELATED APPLICATIONS

This application claims the benefit of and priority to U.S. Provisional Patent Application No. 62/408,499 filed Oct. 14, 2016, the technical disclosures of which are hereby incorporated herein by reference.

TECHNICAL FIELD

The present invention relates general to medical application of lasers and more specifically to stimulation of cellulite reduction by means of laser irradiation of the skin's surface.

BACKGROUND OF THE INVENTION

Cellulite is a herniation of subcutaneous fat within fibrous connective tissue. It manifests itself as dimpling and modularity in the skin particularly in the abdomen and lower body, particularly the thighs and buttocks. Cellulite is more prevalent in women than men and is estimated to affect about 80-90% of post-adolescent women to some degree.

The uppermost layer of subcutaneous tissue (hypodermis) consists of freestanding fat cell chambers filled with fat cells. These are separated by vertical walls of connective tissue called septa. Fibrous connective cords tether the skin to the underlying muscle, with the fat lying between. As fat cells accumulate, they push up against the skin, while the long, tough cords pull down. This creates an uneven surface or dimpling.

The apex of the upright fat chambers are in the form of an arc-like dome that can be prone to collapse under pressure from factors such as excess weight or fluid retention. These larger chambers generate smaller compartments of fat cells (known as papillae adipose) that cluster tightly under the skin. This combination of freestanding fat cell chambers and compartmentalized clusters of fat cells are the elements that create the change in appearance in the skin's surface known as cellulite. As fat cells accumulate, they push up against the skin, while the long, tough cords pull down. This creates an uneven surface or dimpling.

There is a decrease in the number of elastin and collagen fibers in cellulite tissue. It is believed that, as people age, these structural proteins generally begin to stiffen and lose their flexibility. Enlarged fat cells, accumulated fluids and toxins, and poor circulation (both blood and lymphatic flow) can exacerbate the loss of firmness. All of these factors are believed to contribute to the formation of cellulite.

Though excess fat does play a role in the formation of cellulite, reducing cellulite is not merely a matter of losing weight. The disruptions in the connective tissue of the skin that contribute to cellulite's unique appearance must also be addressed. Various forms of treatment for cellulite have been developed including cryolipolysis, massage, ultrasound, radiofrequency irradiation, and lasers, all with varying degrees of success.

Current laser treatments for cellulite involve inserting a laser cannula under a patient's skin and are therefore invasive procedures. The laser light melts the lumpy fat pockets and softens the fiber bands of connective tissue that hold them together. Non-invasive topical laser treatments have also been developed but do not produce photon pulse capable of going deep enough into the skin to stimulate cellular change.

SUMMARY OF THE INVENTION

The invention provides a method and apparatus for stimulating cellulite reduction using a femtosecond diode laser irradiation system. The system comprises a femtosecond diode laser capable of generating laser light that has a wavelength of 1000 nm-10,000 nm, a power level of 300 mw-5 W, and a pulse duration of less than 1 picosecond. In one embodiment the laser light has a wavelength of 1000 nm-1150 nm. In another embodiment the laser light has a wavelength of 1780 nm-10,000 nm.

A light-emitting device is coupled to the diode laser by means of flexible waveguide and is held over the skin. Laser setting controls are set to achieve a depth of photon absorption into the skin to reach subcutaneous adipose tissue.

In one embodiment the light-emitting device is a handheld wand. In another embodiment the light-emitting device is an area pad comprising a plurality of light-emitting lenses on a surface of the pad. In yet another embodiment, the area pad comprises a plurality of pads detachably coupled together.

BRIEF DESCRIPTION OF THE DRAWINGS

The novel features believed characteristic of the invention are set forth in the appended claims. The invention itself, however, as well as a preferred mode of use, further objects and advantages thereof, will best be understood by reference to the following detailed description of an illustrative embodiment when read in conjunction with the accompanying drawings, wherein:

FIG. 3 is a front view of an alternate embodiment of the laser application pad that is longer than the embodiment shown in FIGS. 2A and 2B.

DETAILED DESCRIPTION OF THE DRAWINGS

The present invention provides a laser treatment for stimulating cellulite reduction. The method is based on absorption of light photons through the epidermis, dermis, and subcutaneous tissue layers. This absorption is facilitated by the use of ultrafast laser pulses with duration on the order of femtoseconds.

Figure 1:
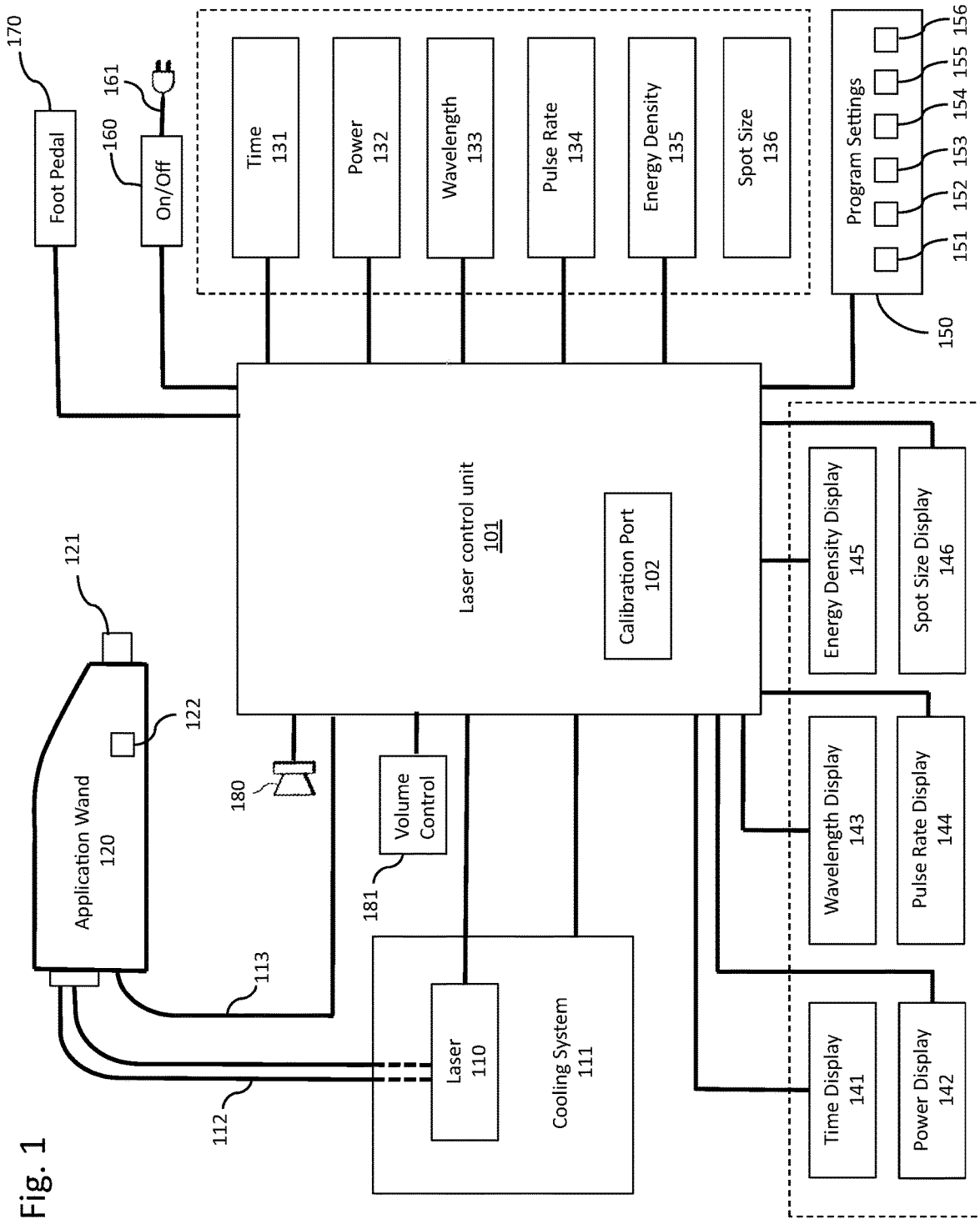
FIG. 1 is a block diagram of a diode laser irradiation system in accordance with an embodiment of the present invention.

FIG. 1 is a block diagram of a diode laser irradiation system in accordance with an embodiment of the present invention. The system includes laser control unit 101 for controlling the operation of a laser 110 that provides therapeutic laser irradiation through a hand-operated probe 120 (or other attachable device) via a flexible waveguide 112.

The control unit 101 receives power through a power supply line 161 adapted for connection to a conventional 120-volt power outlet. An on/off switch 160 is connected in series with the line 161 for controlling the flow of power through the line. A foot pedal 170 is connected to the control unit 101 and is depressible for activating the generation and emission of laser light through the wand 120. Activation may alternatively, or additionally, be provided using a switch 122 on the wand 120.

The system includes laser setting controls 131-136 and corresponding setting displays 141-146. The setting controls 131-136 are utilized to select operational parameters of the control unit 101 according to desired treatment protocols. The setting controls include a treatment time control 131, power control 132, wavelength control 133, pulse rate control 134, pulse density control 135, and laser spot size control 136 in order to achieve the desired therapeutic effects. Adjustments in the operating parameters of the laser 110 utilizing the controls 131-136 make possible improved therapeutic effects based upon the aforementioned treatment protocols involving one or more of these parameters. It is understood that, according to the specific embodiment of the control unit 101, the setting controls may include any combination of one or more of the controls 131-136.

The setting displays include a time display 141, a power display 142, a wavelength display 143, a pulse rate display 144, a pulse density display 145, and a laser spot size display 146. In one embodiment, each of the displays 141-146 comprise light emitting diode (LED) displays such that the corresponding setting controls 131-136 can be operated to increment or decrement the settings, which are then indicated on the displays. A programmed settings controller 150 is used to save setting selections and then automatically recall them for convenience, using one or more buttons 151-156, for example.

The time control 131 adjusts the time that laser light is emitted from the wand 120 from, e.g., 0.01 to 9.99 minutes in 0.01-minute intervals, as indicated on the time display 141. The time display 141 can be set as a countdown display or an accumulated display. Once the time control 131 is set, in countdown mode the time display 141 indicates the setting so that as the wand 120 is operated the time is decremented to zero. In accumulated mode the time display 141 increments from zero (or any other reset value) as the wand 120 is operated so that the total treatment time is displayed. The time display 141 takes into account the pulsed operation of the system.

The power control 132 adjusts the power dissipation level of the laser light in a range from zero up to 12 W, with typical operation ranging from about 500 mw to 1000 mw. The wavelength control 133 allows the operator to tune the wavelength of light generated by the laser 110 depending on the specific application.

The pulse rate control 134 adjusts the pulse rate of the laser 110. The pulse repetition rate (or pulse repetition frequency) $f_{rep}$ of a regular train of pulses is defined as the number of emitted pulses per second. The pulse rate is displayed on the pulse duration display 144 in terms of pulses-per-second (PPS) or repetition frequency. Where as Q-switched solid-state lasers allow repetition rates from below 1 Hz to the order of 100 kHz, mode-locked solid-state lasers (see below) have typically have pulse repetition rates between 1 MHz and 100 MHz.

The energy density control 135 adjusts the energy delivered per unit area, also known as fluence, which is measured in $J/cm^2$ and displayed on the energy density display 145. Typical energy density used might be in the range of about 0.0001 to about 0.0015 joules/$cm^2$.

The spot size control 136 adjusts the focal size of the laser pinpoint. This is typically measured in $mm^2$, which is displayed on the spot size display 146. Spot size, for example, may be 0.5 $mm^2$ to 2 $mm^2$.

An audio volume control 181 is provided for generating an audible warning tone from a speaker 180 when laser light is being generated.

A calibration port 102 is utilized to verify laser performance by placing the wand 120 in front of the port. The port 102 determines whether the system is operating within calibration specifications and automatically adjusts the system parameters.

While not shown, the control unit 101 includes digital and analog electronic circuitry for implementing the foregoing features. The details of the electronic circuitry necessary to implement these features will be readily understood by one of ordinary skill in the art in conjunction with the present disclosure and therefore will not be described in further detail.

In a preferred embodiment of the invention, the laser 110 is a femtosecond laser that emits optical pulses with a duration of below 1 picosecond (ps), i.e., in the domain of femtoseconds (fs) (1 fs=$10^{-15}$ s). Such lasers belong to the category of ultrafast lasers or ultrashort pulse lasers, which are generally defined within the art as lasers with pulse durations on the order of tens of femtoseconds (quadrillionths of a second).

The generation of such ultrashort pulses is typically achieved with the technique of passive mode locking, which is based on the use of a saturable absorber inside the laser resonator. The saturable absorber selectively absorbs low-intensity light and transmits light that is of a sufficiently high intensity. Examples of saturable absorbers for passive mode locking include semiconductor saturable absorption mirrors (SESAMs) and quantum dots (e.g., of lead sulfide) suspended in glass. As light in the resonator cavity oscillates, the saturable absorber selectively amplifies high-intensity spikes and absorbs low-intensity light. This process has the effect of inducing a fixed-phase relationship between the longitudinal modes (standing wave states of excitation) of the laser's resonant cavity. Interference between these modes causes the laser light to be generated as a train of pulses of extremely short duration (i.e. a few femtoseconds).

Examples of diodes used in femtosecond lasers include, but are not limited to, neodymium:glass (Nd:glass), titanium-sapphire (Ti:Sapphire), and ytterbium-doped gain media such as Yb:YAG, yttrium vanadate (Yb:YVO$_4$), Yb:Sr$_3$Y(BO$_3$)$_3$ (aka Yb:BOYS), Yb:GdCa$_4$O(BO$_3$)$_3$ (aka Yb:GdCOB), Yb:glass, e.g. based on silicate or phospate glasses, and monoclinic potassium double tungstates such as Yb:KGW, Yb:KYW and Yb:KLuW.

Due to heat generated during operation, the laser 110 is coupled to a cooling system 111, which removes excess heat from the laser system 110 to avoid overheating critical components. Examples of laser cooling systems that can be used with the present invention include recirculating chillers, liquid-to-liquid cooling systems, ambient cooling systems, cold plates, and heat exchangers, and other laser cooling techniques known in the art.

The critical aspect of femtosecond laser technology is the speed at which the light is fired. The focused ultrashort pulses eliminate the collateral damage of surrounding tissues and the heat generation associated with slower excimer and Nd:YAG lasers, which have longer pulse durations on the order of nanoseconds. Whereas excimer lasers produce precise superficial effects, femtosecond lasers produce precise deeper effects within tissue.

Medical application of femtosecond lasers has been limited primarily to ophthalmology, especially for use in cataract and corneal refractive surgery due to the delicate tissues in the eye. However, the application of femtosecond lasers to other medical fields is relatively unexplored. Furthermore, the use of femtosecond lasers in ophthalmology has been for cutting and ablation. The present invention employs femtosecond laser light at much lower power levels to prevent tissue damage.

The present invention uses femtosecond laser pulses with wavelengths ranging from 1000 nm-10,000 nm to reduce subcutaneous body fat. In one embodiment of the invention the wavelengths used are 1780 nm, 1850 nm, or 2250 nm at a power level of 300 mw-5 W. At these wavelengths, the photons from the femtosecond laser pulses are able to reach the subcutaneous adipose layers to break down the subcutaneous clusters of fat trapped with the fat chambers as well as stimulate the production of collagen and elastin fibers within the connective tissue. The short duration of the femtosecond laser pulses of the present invention produces considerably less discomfort than longer duration pulse lasers even at higher power levels. In addition, the femtosecond pulses produce considerably less collateral tissue damage and stress than that produced by nanosecond lasers such as Nd:YAG lasers.

The laser light can be applied to the skin by means of the hand-held wand 120 for a more localized response. The laser light is supplied to the wand 120 by the laser unit 110 through a flexible waveguide 112. The wand 120 is sized to be easily manipulated by the user. In the example shown in FIG. 1, power is supplied to the wand 120 directly from the control unit 101 via line 113. Alternatively, power may be supplied to the wand indirectly through the laser module 110. In the present example, the wand 120 includes an activator switch 122 that is wired in a suitable manner to the control unit 101 and is used either alone or in conjunction with the foot pedal 170 to activate the laser 110.

The wand 120 has a lens 121 that focuses the laser beam and controls dispersion of the light. In an embodiment, the lens may also be used to adjust the spot size of the laser beam in addition to or as an alternative to the spot size controller 136. In an embodiment, any spot size adjustment made with the lens 121 is displayed on the spot size display 146.

In operation, the switch 160 is closed (i.e., turned on) to power up the control unit 101, at which time the displays becomes illuminated, thereby indicating that the control unit is receiving power. The time control 131 is set for specifying a desired duration of time for laser treatment, which time is displayed on the countdown (or accumulation) display 141. The amount of power is set by the power control 132, and displayed on the power display 142.

The pulse rate control 134 is set for the laser. The pulses-per-second or repetition frequency is displayed on the pulse rate display 144. Depending on the laser unit 110 the wavelength of the laser light may also be tuned and adjusted with controller 133, which is displayed on wavelength display 143. The energy density control 135 is also set and displayed on the energy density display 145. The spot size of the laser may be set with the spot size control 136 and/or the lens 121 on the handheld wand 120 and displayed on the spot size display 146.

It can be appreciated that the laser parameters above are thus selectable for the control unit 101 and are to be determined by the treatment protocols relating to the character of the tissue to be treated, the depth of penetration desired, and the condition of the patient. The audio volume control 181 can be adjusted to control the volume of the tone generated from the speaker 180.

After the laser operating parameters are set, the wand 120 may be directed into the calibration port 102 to verify the accuracy of the system. The wand 120 may then be applied to patient tissue for therapy. The foot pedal 170 and/or the wand switch 122 may be depressed to cause therapeutic laser light energy to be generated from the wand 120. To indicate that laser light energy is being generated, an audible tone is generated from the speaker 180.

The generated laser optical energy is applied to target regions of the body (i.e. cellulite pockets). The surface of the tissue in the region to be treated is demarcated to define an array of grid treatment points, each of which points identifies the location of an aforementioned small treatment area. Each small treatment area is irradiated with the laser beam light to produce the desired therapeutic effect. The energy of the optical radiation is controlled by the power control 131 and applied as determined by treatment protocols. The laser beam wavelength, spot or beam size, power dissipation level, and time exposure are thus carefully controlled to avoid damaging the tissue from thermal effects.

Figure 2A:
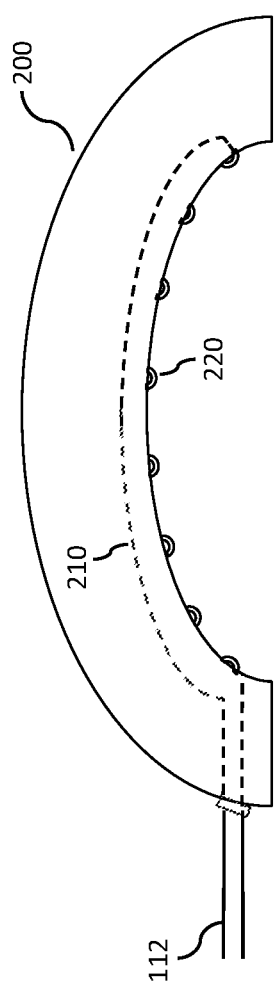
FIG. 2A is a top, cross-section view of a laser application area pad in accordance with an embodiment of the invention.
Figure 2B:
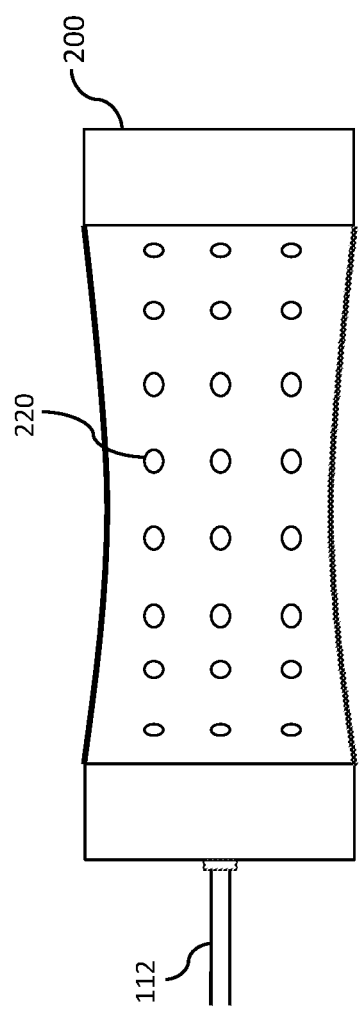
FIG. 2B is a front view of the laser application pad.

FIG. 2A is a top, cross-section view of a laser application pad in accordance with an embodiment of the invention. FIG. 2B is a front view of the laser pad. The pad 200 shown in FIGS. 2A and 2B is roughly half-moon shaped is and designed to be placed over an area of the body such as the torso or limbs and secured in place by an adjustable strap for other suitable method known in the art. The pad can be made from any pliable material that will hold its shape such as foam. It should be noted that FIGS. 2A and 2B are not drawn to scale.

The purpose of the pad 200 is to distribute and apply laser light to broader surface area of the skin than is possible with the handheld wand 120. This capability makes it easier to stimulate a more general physiological response in the tissue than is possible with the wand.

In the embodiment shown in FIGS. 2A and 2B, the pad 200 attaches to the flexible waveguide 112 from the laser 110 in place of the wand. The external waveguide 112 in turn is coupled to an internal waveguide 210 within the pad 200. Alternatively, the pad 200 may have its own external waveguide already build in which is then coupled to the laser 110. Laser light transmitted through the internal waveguide 210 is emitted through a plurality of lenses 220 on the inner surface of the pad 200. The distribution and placement of lenses 220 shown in FIGS. 2A and 2B is merely an example and is not intended to be limiting. The distribution of lenses will be determined by several factors including the size of the pad 200, area of the body, lens size, and the amount of light dispersion created by the choice of lens.

FIG. 3 is a front view of an alternate embodiment of the laser application pad that is longer than the embodiment shown in FIGS. 2A and 2B. The longer pad 300 is suited for application to limbs such as the thighs or arms, particularly for taller patients.

Figure 4:
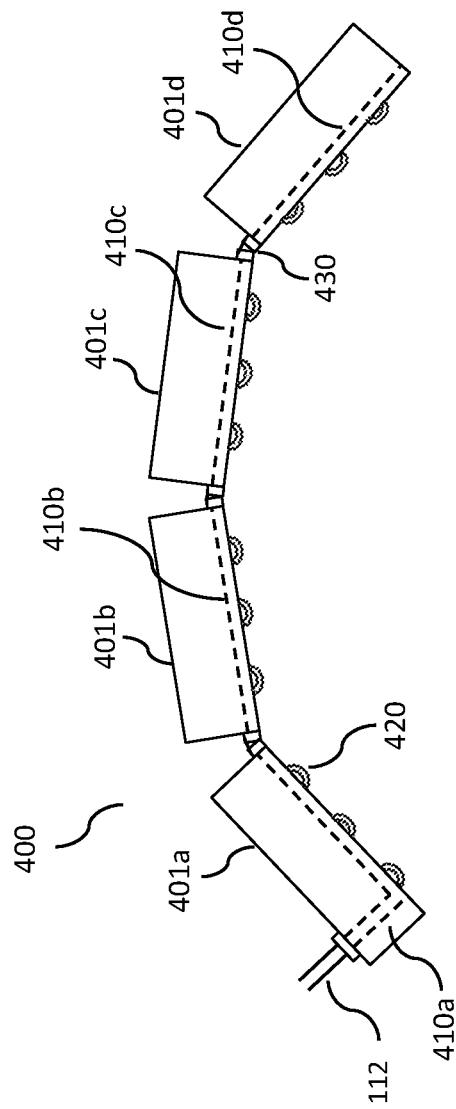
FIG. 4 is a top, cross-section view of a modular version of the laser application pad in accordance with an embodiment of the invention.

FIG. 4 is a top, cross-section view of a modular version of the laser application pad in accordance with an embodiment of the invention. This version of the pad provides flexibility in sizing. In the example shown, the pad 400 is composed of three panels 401a, 401b, 401c, and 401d, which may be fastened together using Velcro® or similar attachments means. The number of panels assembled together will vary according to the size of the individual panels, the size of the patient, and the area of the body to be treated. It should be noted that FIG. 4 is not drawn to scale and is provided for purposes of illustration.

Like the embodiments shown in FIGS. 2A, 2B, and 3, the panel 401a has an internal waveguide 410a that is coupled to an external waveguide 112 from the laser source 110.

Alternatively, the panel 401a may have its own external waveguide already build in which is then coupled to the laser 110.

The internal waveguide 410a in panel 401a is in turn coupled to the internal waveguides 410b, 410c, and 410d of panels 401b, 401c, and 410d, respectively, by means of a flexible connectors 430. Laser light from the waveguides 410a, 410b, 410c, 410d is emitted through the lenses 420 on the inner surface of the panels. The flexible attachment of the panels allows the modular laser pad 400 to be folded around the limb or body segment to be treated and allows a more customized fit than a pre-shaped pad.

Because cellulite may have an uneven distribution treatment may involve both spot treatments with the wand 120 and general area treatments using the one of the pads 200, 300, or 400 described above.

The description of the present invention has been presented for purposes of illustration and description, and is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated. It will be understood by one of ordinary skill in the art that numerous variations will be possible to the disclosed embodiments without going outside the scope of the invention as disclosed in the claims.

We claim:

1. A method for stimulating cellulite reduction using a diode laser irradiation system, the method comprising:
    selecting an area of skin;
    placing a foldable, light-emitting device over the area of skin to partially surround the area of skin, the foldable, light emitting device coupled to a femtosecond diode laser and operable to emit coherent light generated by the femtosecond diode laser;
    irradiating the area of skin with laser light from the femtosecond diode laser that has a wavelength of 1000 nm-10,000 nm, a power level of 300 mw-5 W, and a pulse duration of less than 1 picosecond; and
    operating the femtosecond diode laser, using laser setting controls of the system, to achieve a depth of photon absorption into the area of skin to reach subcutaneous adipose tissue.

2. The method according to claim 1, wherein the wavelength is 1000 nm-1150 nm.

3. The method according to claim 1, wherein the wavelength is 1780 nm-10,000 nm.

4. The method according to claim 1, wherein the foldable, light-emitting device is a handheld wand.

5. The method according to claim 1,
    wherein,
        the foldable, light-emitting device includes at least one area pad with a portion of an internal waveguide extending at least partially through the at least one area pad,
        the at least one area pad coupled to a plurality of light-emitting lenses, and
        the plurality of light-emitting lenses are positioned on a surface of the at least one area pad.

6. The method according to claim 5,
    wherein,
        the at least one area pad includes a plurality of pads detachably and rotatably coupled together, and
        each of the plurality of pads include a set of the plurality of light-emitting lenses.

7. A diode laser irradiation system for stimulating cellulite reduction, the system comprising:
    a femtosecond diode laser operable to generate laser light with a wavelength of 1000 nm-10,000 nm, a power level of 300 mw-5 W, and a pulse duration of less than 1 picosecond;
    a foldable, light-emitting device configured to be positioned over an area of skin and to partially surround the area of skin, the foldable, light-emitting device coupled to the femtosecond diode laser by a flexible waveguide and operable to emit coherent light generated by the femtosecond diode laser; and
    laser setting controls operable to control the femtosecond diode laser to achieve a depth of photon absorption into the area of skin to reach subcutaneous adipose tissue.

8. The diode laser irradiation system according to claim 7, wherein the wavelength is 1000 nm-1150 nm.

9. The diode laser irradiation system according to claim 7, wherein the wavelength is 1780 nm-10,000 nm.

10. The diode laser irradiation system according to claim 7, wherein the light-emitting device is a handheld wand.

11. The diode laser irradiation system according to claim 7,
    wherein,
        the foldable, light-emitting device includes at least one area pad with a portion of an internal waveguide extending at least partially through the at least one area pad,
        the at least one area pad is coupled to a plurality of light-emitting lenses, and
        the plurality of light-emitting lenses are positioned on a surface of the at least one area pad.

12. The diode laser irradiation system according to claim 11,
    wherein,
        the at least one area pad includes a plurality of pads detachably and rotatable coupled together, and
        each of the plurality of pads include a set of the plurality of light-emitting lenses.

* * * * *